United States Patent [19]

Graham

[11] Patent Number: 5,085,033

[45] Date of Patent: * Feb. 4, 1992

[54] PROCESS FOR PREPARING A SOLID ENCAPSULATED MEDICAMENT

[75] Inventor: Dean M. Graham, Hobart, N.Y.

[73] Assignee: D. M. Graham Laboratories, Inc., Hobart, N.Y.

[*] Notice: The portion of the term of this patent subsequent to Jun. 26, 2007 has been disclaimed.

[21] Appl. No.: 544,183

[22] Filed: Jun. 26, 1990

Related U.S. Application Data

[63] Continuation-in-part of Ser. No. 7,272,734, Nov. 17, 1988, Pat. No. 4,936,074.

[51] Int. Cl.⁵ .................. B65B 7/28; B65B 63/08; A61K 9/64
[52] U.S. Cl. ........................ 53/436; 53/440; 53/471; 53/900; 424/454
[58] Field of Search ............... 53/400, 436, 440, 467, 53/471, 474, 477, 478, 900; 424/451, 454, 456; 426/138

[56] References Cited

U.S. PATENT DOCUMENTS

| | | | |
|---|---|---|---|
| 3,432,592 | 3/1969 | Speiser | 264/328.18 X |
| 4,028,024 | 6/1977 | Moreland | 53/900 X |
| 4,163,354 | 8/1979 | Austin | 53/436 |
| 4,497,157 | 2/1985 | Dürr et al. | 53/440 X |
| 4,591,475 | 5/1986 | Tomka et al. | 264/328.14 |
| 4,655,840 | 4/1987 | Wittwer et al. | 106/126 |
| 4,673,438 | 6/1987 | Wittwer et al. | 264/328.18 X |
| 4,734,149 | 3/1988 | Brown | 53/478 X |
| 4,928,840 | 5/1990 | Barshay et al. | 424/451 X |
| 4,936,074 | 6/1990 | Graham | 53/900 X |

*Primary Examiner*—Robert L. Spruill
*Assistant Examiner*—Linda B. Johnson
*Attorney, Agent, or Firm*—Klauber & Jackson

[57] ABSTRACT

The present invention relates to the preparation of encapsulated products containing a solid dosage form prepared with up to 35% of an edible matrix material. The composition may be introduced into the capsule as a powder and the capsule containing the powder mixture may then be heated to melt the matrix. The resulting capsule products exhibit the favorable texture of a capsule in conjunction with the hardness, shelf stability and security of the solid formulation. The composition of the present invention may be prepared and used as a direct tableting granulation as well as the filler or core for the capsule product. A method and corresponding apparatus are likewise disclosed and contemplated herein.

19 Claims, No Drawings

PROCESS FOR PREPARING A SOLID ENCAPSULATED MEDICAMENT

CROSS REFERENCE TO RELATED APPLICATION

The present application is a continuation-in-part of co-pending application Ser. No. 07/272,734 filed Nov. 17, 1988 now U.S. Pat. No. 4,936,074, issued June, 26, 1990 by the inventor herein.

BACKGROUND OF THE INVENTION

The present invention relates generally to encapsulated products containing edible active ingredients such as medicaments, foods and the like, and more particularly, to encapsulated products that offer improved security in combination with extended shelf life and physical integrity.

The products with which the present invention is concerned comprise encapsulated ingestible materials that have been in broad use and distribution for many years. Such encapsulated products have been prepared by the placement of flowable materials whether in powder or liquid form within the capsule structure which is generally prepared as two telescoping capsule halves. Accordingly, the contents of the encapsulated product are located within the capsule halves, and the capsule halves are then brought together into telescopic engagement and are thereafter sealed, whereupon the contents of the capsule are secured. Generally, such capsules are employed in the pharmaceutical and food industries and hold various edible and pharmaceutically active materials, such as medicines, vitamin preparations, and the like. The materials from which the capsule halves are prepared are usually hydrophilic, and are thereby adapted to dissolve in the intestines after ingestion. One of the prevalent difficulties and drawbacks to the use of capsules in the manner stated above has been their tendency to disengage and to prematurely release their contents. Accordingly, the prior art contains numerous disclosures directed to the establishment and maintenance of a sealing engagement between the capsule halves.

The problem of this engagement became more acute during the early part of this decade with the advent of the deliberate disengagement of encapsulated medicaments and the placement therein of certain poisons. Such deliberate activity was possible because of the inadequate sealing engagement between the capsule halves, and resulted in the decision by several of the major pharmaceutical firms to abandon the use of capsules as a dosage form for their medicaments. As a result, the pharmaceutical industry moved toward the use of a solid dosage form which externally resembled the capsule and which was known as the caplet. This dosage form, however, has met with limited consumer acceptance, and as a result, the manufacturers have now attempted to remedy this situation by the placement of a coating or capsule about the solid caplet, in an effort to improve the organoleptic properties of the dosage form.

A variety of techniques are therefore in use for the preparation of this composite solid dosage form, including the initial preparation of the caplet followed by the dipping, spraying or other application of an outer coating such as gelatin, and the friction-fit application of hollow capsules to the rigid caplets. Both of these approaches are time-intensive and frequently result in a product that is inadequate both commercially and for security reasons. The ability of the capsule halves to be dislodged from each other remains with the result that one can tamper with this solid dosage form and dispose a poison interstitially between the capsule half and its contents.

In addition to the shortcomings of the processes in use presently, Applicants have reviewed other literature relating to this subject and find no disclosures in the prior art respecting the products and corresponding processes of the present invention. For example, U.S. Pat. No. 3,432,592 to Speiser discloses the injection molding of an oral medicament in solid form, utilizing thermoplastic synthetic resins that are either insoluble or are of limited solubility, in large quantities for the purpose of developing delayed-release formulations. The resins used by Speiser include both polycondensation and polyaddition resins which are present in amounts of from 60% to 80% of the total tablet content. The temperature at which these materials are processed is substantially elevated and, for example, ranges upwards of 80° C. to 160° C. Such formulations, however, because of their limited solubility and composition are only useful in the instance where delay in release of the active ingredient is desired. Moreover, the elevated temperature at which the materials are processed would result in an undue amount of loss or attenuation of the active ingredients most commonly formulated by encapsulation, as the ingredients would either break down or would flash off at these temperatures. Accordingly, the disclosure of Speiser does not offer a solution to the problems faced in the capsule art as to the development of prompt release encapsulated materials offering desired organoleptic properties.

U.S. Pat. No. 4,082,024 to Moreland represents an alternative to conventional encapsulation wherein the contents of the capsule and the capsule material are co-extruded and then formed into capsule shapes. The Moreland disclosure relates primarily to the formation of an encapsulated product by the simultaneous disposition of the contents of the capsule and the capsule-forming materials in a continuous cylindrical mass which is then individually out and shaped to form the encapsulated product. Nothing in Moreland discloses the use of conventional preformed capsules or the preparation of a solid product including solidified capsule contents.

The remaining prior art comprising U.S. Pat. Nos. 4,673,438; 4,591,475; and 4,655,840 all relate to the manufacture of the capsule halves by injection molding techniques, including reference to appropriate capsule-forming compositions. Nothing in these disclosures relates to the formation of solid encapsulated dosage forms and therefore offers no suggestion to the artisan with respect to the problems faced and to appropriate solutions.

The need therefore exists for the development of a solid encapsulated dosage form offering the desired organoleptic properties of an encapsulated product in combination with the security and shelf stability afforded by a solid dosage form.

In co-pending application Ser. No. 07/272,734, the disclosure of which is incorporated herein by reference, a method for the preparation of an improved solid encapsulated product was disclosed. This product provides a solid encapsulated dosage form offering the desired organoleptic properties of an encapsulated product in combination with the security and shelf stability afforded by a solid dosage form. The present disclosure covers an alternate method for the preparation of the inventive dosage form that provides a product having all of the improved properties attainable in accordance with applicant's earlier disclosure.

SUMMARY OF THE INVENTION

In accordance with the present invention, a solid encapsulated product for the peroral delivery of medicaments and other edible agents is disclosed which comprises a capsule shell and a composition adherently disposed therein in solid form, the solid composition comprising an active ingredient selected from the group consisting of pharmaceutical compounds, vitamins, food ingredients and comestibles, and a matrix material present in an amount of up to about 35% by weight of the said solid composition and having a melting point of up to about 100° C. The solid composition is initially prepared as a direct flowable mixture of the active ingredient and the matrix material. This mixture is then placed into the empty capsule halves, and is preferably densely packed. The filled capsules are closed and then carefully heat treated to melt the matrix, after which the capsules are cooled to harden the matrix.

Accordingly, the present invention further includes a method for the preparation of a solid encapsulated product comprising preparing the flowable mixture of the active ingredient with the ingestible matrix material, filling an ingestible hollow capsule with the flowable mixture material in an amount sufficient to substantially completely fill the interior thereof, closing the thus filled capsule and heating the filled capsule to a temperature sufficient to liquify the matrix but insufficient to impair the structural integrity of the capsule and the chemical stability of the active ingredient, and thereafter solidifying the mixture in the sealed capsule to form the solid encapsulated product. After the capsules are filled, the compositions may be solidified by cooling to room temperature, whereupon the matrix material would harden.

As indicated earlier, the matrix materials suitable for the present invention are edible materials having a melting point ranging up to about 100° C. and preferably, from about 60° C. to about 100° C. Suitable matrix materials include carbohydrates such as sorbitol and mannitol, polyalkylene glycols such as the carbowaxes, polyoxyalkylene glycols, and mixtures thereof. More particularly, the matrix material may be selected from sugar alcohols such as mannitol and sorbitol, gelatin, mannose, and polyethylene glycols having an average molecular weight ranging from about 6,000 to about 10,000.

In a particular embodiment, a mixture of gelatin and a polyethylene glycol having a molecular weight in the aforestated range may be used to achieve a combination of solidification and adherence to the outer capsule, particularly in the instance where the outer capsule is prepared from gelatin. Further, gelatin alone containing 20% water can be used as the matrix and will achieve a combination o solidification and adherence to the outer capsule, particularly in the instance where the capsule is prepared from gelatin.

In a preferred embodiment, the matrix material is present in an amount by weight of the composition ranging from about 5% to about 20%, and more preferably, from about 15% to about 20%.

A further aspect of the present invention is the improvement in security that is gained by the use of the melt formation of the encapsulated solid dosage form. The products thus prepared are tamper evident as the capsules can only be dislodged by heat and will irreversibly deform. Added security through improved bonding of the capsule to its contents can be achieved by preliminarily wetting the interior surface of the capsule with a gelatin solution, water or methanol, and applying to the wetted surface an amount of granular gelatin sufficient to form a roughened wall surface. For example, the wetted surface could be given a dusting of the gelatin granulate that would promptly adhere thereto. The roughened surface would become embedded in the solidified composition thereafter introduced therein, and would offer further resistance to removal of the capsule from the solid core.

The present invention may be practiced with suitable apparatus for the practice of the present method comprising a capsule filling machine including die plates or other mechanisms holding the hollow capsule halves and capsule content delivery means.

After assembly, the capsule contents could be dried and sealed by the application of mild heat energy such as by electromagnetic radiation, whereupon the capsule halves would be welded to each other and the matrix material would likewise bond to the interior of the capsule walls.

The capsule products prepared in accordance with the present invention offer several advantages over capsule products presently commercially available. Particularly, the present capsule products offer the security and tamper resistance and evidence available only with solid dosage forms, in combination with the texture and other sensory attributes available only with the use of encapsulated dosage forms. The encapsulated products are likewise advantageous in that they offer improved shelf stability and durability by virtue of the solidification of the capsule contents. The manufacture of the present encapsulated product is simpler and more economical than prior art processes for the preparation of acceptable solid dosage forms and is likewise more rapid.

Accordingly, it is a principal object of the present invention is to provide a solid encapsulated dosage form for an edible ingredient or medicament which is capable of utilizing conventional capsule technology.

It is a further object of the present invention to provide a solid encapsulated product as aforesaid that offers a combination of tamper evidence and improved sensory attributes.

It is a still further object of the present invention to provide encapsulated solid dosage form as aforesaid that is economical and may be rapidly prepared.

It is a still further object of the present invention to provide a method for the manufacture of an encapsulated solid dosage form which is simple and rapid to practice.

It is a still further object of the present invention to provide an apparatus for the practice of the method of the present invention that is capable of rapid and economical operation.

Other objects and advantages will become to those skilled in the art from review of the ensuing detailed description.

DETAILED DESCRIPTION

In accordance with the present invention, an encapsulated solid product for the dosage delivery of an edible active ingredient such as a medicament, food, confection or the like comprises a hollow ingestible capsule shell containing a solidified composition disposed adherently therein, which composition comprises the active ingredient selected from the group consisting of pharmaceutical compounds, vitamins, food ingredients and comestibles, and a matrix material which is present in an amount of up to about 35% by weight of the composition and has a melting point of up to about 100° C. More particularly, the matrix material is present in an amount ranging from about 5% to about 35% by weight, and is preferably present in an amount of from about 10% to about 20%. The matrix material has a melting point ranging from about 60° C. to about 100° C. The matrix material serves to solidify the composition and to thereby render it resistant to tampering and premature disintegration.

The product and associated method of the present invention are based upon a procedure of direct melt formation. Accordingly, the solid composition comprising the active ingredient(s) and the matrix is formed by the melting of the matrix in direct contact with the active ingredient(s) and the consequent coating of the latter by the melted matrix material, and not by the formation of a solution of the matrix which is then combined with the active ingredients. The present procedure is advantageous as it reduces the components that must be included during the preparation of the composition, as well as the number and complexity of the processing steps that are involved. For example, the absence of solvents eliminates the need for solvent evaporation and drying of the composition and the concomitant exposure of the composition to temperatures that may adversely affect the stability of the active ingredient(s).

The composition as prepared may be easily formed either into a solid dosage form directly from the melt stage such as by the filling of capsule which are thereafter merely cooled to solid state, or may be milled into a dry powder which can then be either dry filled and packed into capsules and thereafter heated to harden the capsule contents, or directly compressed into a solid dosage form.

Suitable matrix materials are edible and hydrophilic, as well as hydrophobic, and include carbohydrates, polyalkylene glycols, polyoxyalkylene glycols, and mixtures thereof. More particularly, the matrix material may be selected from polyethylene glycols, polyoxyalkylene glycols, sugars, sugar alcohols, gelatin and mixtures thereof. Accordingly, suitable matrix materials include sugars such as mannose, glucose, galactose, fructose, arabinose, xylose, sucrose, maltose and others. Suitable sugar alcohols include erythritol, arabitol, xylitol, adonitol, mannitol, dulcitol, sorbitol and mixtures.

The matrix may also be prepared from various polyethylene glycols known by a variety of trade names such as Carbowax, PEG, Pluricol E, Poly-G, Polyglycol E and the like. These compounds all have the general formula $H(OCH_2)CH_2)_nOH$, where n is greater than 4. These compounds have previously been used as water soluble lubricants for molds and fibers and in metal-forming operations as well as in food and food packaging. The polyethylene glycols useful in accordance with the present invention have an average molecular weight ranging from about 6,000 to about 20,000 and an average n value exceeding 158. The preferred polyethylene glycol of the present invention is known as Carbowax 8000, which is known to have a melting point of from 60° C. to 63° C. This melting temperature is particularly significant, as it is below the temperature of most of the medicaments and other active ingredients that are encapsulated in accordance with the present invention. This lower temperature thereby assures that the composition of the present invention may be prepared and liquified to the extent necessary to liquify and thereafter harden the same within the gelatin capsule without reaching a temperature that would be deleterious to the stability, efficacy or toxicity of the active ingredient to be included in the solid dosage form, or the structural integrity of the capsule itself.

More particularly, the matrix material of the present invention may comprise sugars such as mannose, sugar alcohol such as mannitol and sorbitol, and the polyethylene glycol known as Carbowax 8000. Further, the polyalkylene glycol such as the polyoxyethylene glycols or polyethylene glycol ethers are also useful herein.

While the matrix may melt at temperatures of as high as 100° C., the temperature used in the instance where the composition is melted in the gelatin capsule should not cause the capsule to exceed its softening temperature, since as mentioned above, this would cause undesirable deformation and distortion of the capsule wall. Such distortion if evident on a previously completed product would reveal tampering, as the contents of the present encapsulated product cannot otherwise be accessed except by heating and removal of the capsule shell. This temperature sensitivity resulting from the adhesive bond between the capsule and its contents provides a further security feature hereof.

The melting or softening temperature of the matrix material may be controlled by the addition of impurities or other melt temperature modulating agents. Such agents should be edible and may be water soluble. For example, the melting temperature of sorbitol may be depressed by the addition of a quantity of glucose, such as set forth in tabular form below.

| SOFTENING TEMPERATURES OF SORBITOL-GLUCOSE BLENDS | | |
|---|---|---|
| GLUCOSE (%) | SORBITOL (%) | SOFTENING TEMP. (°C.) |
| 2% | 98% | 75° C. |
| 4% | 96% | 74° C. |
| 6% | 94% | 72° C. |
| 10% | 90% | 68° C. |
| 15% | 85% | 66° C. |
| 20% | 80% | 61° C. |

Other materials useful as melt temperature modulators may include for example, glycerine, lower molecular weight polyethylene glycols, and the like, it being understood that the modulator like the matrix material, must be edible and preferably water soluble.

In addition to the active ingredient and the matrix material, the composition of the present invention may include other conventional ingredients such as excipients, disintegrants, binders and extenders. Accordingly, ingredients such as cellulose ethers and esters, calcium carbonate, talcum powder, bentonite, alumina, magnesium silicate, magnesium stearate, corn starch, sodium lauryl sulfate, and the like, are contemplated. Particular disintegrants useful in accordance with the present invention are corn starch and a material known as Ac-Di-Sol. The disintegrants may be included in amounts of up to about 20% by weight depending upon the nature of the matrix material and the speed of disintegration that is desired.

In addition to utilizing the composition of the present invention for the preparation of the encapsulated products as defined herein, the composition may also be used for direct compression tableting. In such instance, lubricants such as sodium lauryl sulfate and the like would be added, unless polyethylene glycol is used which is itself a lubricant.

The method of the present invention comprises the preparation of the mixture of the active ingredient in the composition including the matrix material and other standard additives. This mixture is then introduced into the hollow capsule in powder form after which the capsule halves are closed, heat is applied to melt the matrix and after cooling, the resulting hard encapsulated product is obtained. The mixture is heated to a temperature sufficient to liquify the matrix material but inadequate to damage the active ingredient by causing the flashing off or breakdown of the same. Typically, the mixture may be heated to a temperature ranging from about 60° C. to about 70° C., whereupon the matrix material will liquify. Thus, in one embodiment, the powder composition may first be introduced in dry and cooled form into the hollow capsule halves, the capsule may then be assembled and the assembled capsule subject to heating either by conventional convection means or by dielectric means, to cause the selective melting of the matrix and the hardening of the capsule contents.

As mentioned earlier, the matrix and the active ingredients may be co-extruded and thereafter granulated, as would be the case if a compressible mixture were to be prepared, after which this granulate could be directly filled into capsules. In such event, the granulate would not contain the normal ingredients that would be utilized in the instance where direct compression is anticipated. The processing conditions for the formation of the granulate would otherwise be the same.

In an alternative embodiment of the invention, the composition would be prepared as indicated by mixing the active ingredients and the matrix, followed by the introduction of the mixed composition into the capsule halves. In this embodiment, the capsule halves would be filled by a technique known as capsule filling, which may in one embodiment utilize conventional capsule filling equipment preferably having tamping rods. Such equipment operates on the basis that a quantity of the capsule contents is first introduced into the capsule, after which the tamping rods are directed into the partially filled capsule to compact the capsule contents. The procedures of incremental filling and compacting are conducted alternatively and repeatedly until the capsule is completely filled. In this way, the capsule bodies are filled to a maximum density and compactness.

In accordance with the present invention, the tamp filling operation is conducted at an elevated temperature, for example, with the tamping rods heated so as to effect a localized melting of the matrix through each tamping cycle. Also, the composition may be preheated to a temperature just below the level at which the matrix will melt, to facilitate rapid melting when the composition is placed into the capsule half and tamped with a heated tamping rod. When the capsule half is completely filled, and an inspection of the capsule contents may be made, it will be found that capsule contents are densely packed and have formed a solid mass owing to the repeated application of localized elevated temperature sufficient to cause the melting and fusion of the matrix.

In such instance, and in accordance with a particular embodiment of the invention, the telescoping capsule cover or cap may likewise have introduced thereinto a quantity of the composition, likewise subjected to heated tamping, so that upon uniting the capsule halves, a maximum quantity of compacted contents is achieved. The capsule thus prepared may be further exposed to brief heating either by convection or by electromagnetic wave energy radiation, to achieve a final fusion, of the capsule contents into the solidified form desired.

After the filling of the capsule base, the capsule cap may then be introduced thereover to telescopically receive the former, whereupon the completely filled and assembled capsule product may be ejected and transferred for drying and solidification of the capsule contents. Drying may be effected by room temperature cooling, or by the application of further reduced temperature. After solidification, the capsules may be subjected to the further processing wherein the capsule contents may be permanently bonded to the interior of the capsule walls, as by the application of electromagnetic wave energy radiation. In the instance where the matrix includes a quantity of gelatin, adherence of the capsule contents to the capsule walls is enhanced.

The hardened capsule formed as indicated above may be subjected to a further capsule sealing step wherein the exterior of the capsule is first sprayed with a dielectric fluid and is thereafter exposed to electromagnetic wave energy, to effect a welding or sealing of the capsule halves, all in accordance with the teachings of U.S. Patent No. 4,820,364, issued April 11, 1989 to Dean M. Graham, the disclosure of which is incorporated herein by reference. Alternatively, other forms of post processing of capsules to make them tamper evident, such as capsule banding, may be employed, and the present invention is not strictly limited to any particular post processing step.

In accordance with the present invention, an apparatus may be prepared for the practice of the present method which would involve a standard capsule-filling machine of the type described earlier. In the present instance, the capsule-filling machine may be the conventional variety for direct capsule filling, or, in the instance where tamp filling is contemplated, may be a conventional tamp filling machine. In the instance of tamp filling, the machine may be modified to apply a heating means to the tamping rods, to achieve the elevated temperatures desired. In such instance, and by way of example, the tamping rods may be associated with magnetic wave energy heating means, and, for example, may be heated to a temperature of 90° C., to convey an adequate quantity of heat to the compressible composition as it resides in the capsule during the filling process. Naturally, other heating means are contemplated, and the invention is not limited particularly to the operation or construction of the apparatus in this fashion.

The apparatus contemplated in accordance with the present invention would be able to operate at the same speed as conventional capsule filling apparatus, thereby offering comparable economy and speed of manufacture in conjunction with an improved encapsulated product. Moreover, the contemplated apparatus facilitates the development of higher speed encapsulating equipment.

Accordingly, the apparatus of the present invention may comprise known capsule filling machines made by companies such as Elanco, Roto-Fils, Fratelli Zanosi and other comparable known apparatus. In each instance, the hopper provided for the dispensing of the flowable granular material conventionally contained in capsules may be replaced with either an extrusion unit or an injection molding unit adapted to communicate with the plate holding the empty capsule bases, so that the appropriate quantity of flowable composition is dispensed directly therein. Naturally, the foregoing discussion is presented by way of example only, as modifications to the apparatus contemplated in accordance with the present invention may be made within the scope hereof.

The present invention will be further illustrated by reference to the following illustrative examples wherein all percentages, unless otherwise specified, are to be considered as percentages by weight.

EXAMPLE 1

In this initial experiment, the feasibility of the present method was explored and confirmed. Accordingly, 100 grams of a dense grade of acetaminophen (hereinafter APAP) and 15 grams of Carbowax 8000 were weighed out and placed in a beaker, and then subjected to heating to a temperature above 60° C., whereupon the mass became dense with the melted Carbowax. The material was then placed in empty size No. 1 maroon capsule bodies, and the damp mass was pressed into the capsules, after which caps were placed over the filled capsule bases and fully applied into the closed position. Ten capsules were prepared in this fashion and then set aside to cool at room temperature.

The completed capsules were weighed and their weights compared in relation to empty capsules. The empty capsules were noted to have a weight of 75 mg. per capsule, whereas the weighted capsules had weights of 684, 666, 675, 660, 658, 680, 672, 675, 662 and 681 mg., respectively. The average weight of the filled capsule was thereby determined to be approximately 671.3 mg., so that the content was determined thereby to be 596.3 mg.

The cooled capsules were then inspected and were found to be desirably hard. The capsules were subjected to disintegration and disintegrated within 12 minutes. Certain of the capsules were further exposed to bonding by placement in a microwave held at ¾ power for 50 seconds. The resulting bond was good. A comparison of the properties of the bonded and unbonded capsules was then made, whereupon it was attempted to remove the capsule cap from the capsule body. This was possible in the case of the unbonded capsule, although, the contents of the capsule could not be removed from the remaining capsule half. In the instance where the capsules were subjected to bonding, the capsule halves could not be separated.

EXAMPLE 2

Further formulations were prepared seeking to determine the operability of varying quantities of the matrix material. Accordingly, four formulations were weighed out as set forth in Table 1, below.

TABLE 1

| INGREDIENTS | FORMULATION (in grams) | | | |
|---|---|---|---|---|
| | 1 | 2 | 3 | 4 |
| APAP - Dense | 100 | 100 | 100 | 100 |
| Carbowax 8000 | 5.26 | 11.11 | 17.6 | 25 |

Formulations 1–4 correspond to matrix contents of 5%, 10%, 15% and 20%, respectively.

The materials were blended and subjected to 60° C. heat until the matrix melted, whereupon equal quantities of the composition were introduced into capsules and filled and sealed as before. All of the capsules thus prepared produced hard cores with the exception of the formulation including 5% of Carbowax 8000 alone, which was of lesser hardness although operable. It was noted that as the percent of matrix increased, the melt was more plastic and easier to manipulate.

EXAMPLE 3

The disintegration of the encapsulated products prepared in accordance with the present invention was examined further by the addition of a disintegrant and the observation as to the effect that such disintegrant had upon disintegration time as well as the other properties of the encapsulated product. Thus, all the capsules were subjected to disintegration, and it was noted that disintegration took place within a maximum of 20 minutes, with the capsules prepared with 5% Carbowax disintegrating within 5 minutes, and the capsules containing 20% of the matrix Carbowax disintegrating within 19 minutes.

The preparation of specimens with 15% matrix and an included quantity of the disintegrant Ac-Di-Sol produced a reduction in the disintegration time. In particular, in the instance where 400 mg. of Ac-Di-Sol was added to 20 grams of a 15% composition blend, the disintegration time dropped from 16 minutes to 12 minutes. In the instance where 800 mg. of Ac-Di-Sol was added to a similar quantity of 15% matrix material, the disintegration time dropped from 16 minutes to 4 minutes. The capsules thus prepared had been inspected prior to conducting the above disintegration tests, and were found to be sufficiently solid and to thereby possess all of the desired properties of encapsulated prepared in accordance with the present invention.

EXAMPLE 4

Further studies of disintegration including a disintegrant were carried out, and in this instance, 100 grams of APAP, 15 grams of Carbowax 8000, and 2.3 grams of Ac-Di-Sol were blended. The APAP and Carbowax were first blended and melted and thereafter reblended, after which the Ac-Di-Sol was added and further blending took place. Equal quantities of the resulting mixture were placed in six size No. 1 capsules, weighed and tested for disintegration. All capsules were noted to contain over 588 mg. of material of which 500 mg. constituted APAP. Disintegration of the capsules thus prepared was approximately 5 minutes 32 seconds, and it was thereby determined that a size No. 1 capsule could be successfully filled with 500 mg. of APAP as a solid core utilizing a composition having the following ratio of ingredients with respect to each other: Ratio of APAP to Carbowax 8000 to Ac-Di-Sol = 100:15:2.3.

EXAMPLE 5

The composition of the present invention was formulated and tested for use as a direct compression formulation, i.e., a formulation which is directly used in the manufacture of tablet dosage units. Accordingly, test tablets were prepared having 5%, 10%, 15% and 20%, respectively of Carbowax 8000 and APAP Stock No. C0004. The respective formulations were then prepared into tablets on a Code 10—10 tablet press. The resulting tablets were all excellent.

EXAMPLE 6

Filled capsules containing the composition of the present invention were prepared wherein the APAP component is selected from capsule grade rather than dense material. Accordingly, 1 kg. of capsule grade APAP (Stock No. C0309) and 150 grams of Carbowax 8000 were weighed out and blended on a Hobart blender. The material was then placed in an oven set at 60° C. for two hours. Thereafter, the material was re-blended on a Hobart blender and returned to the oven for 20 minutes at the same temperature. After this second heating, the material was test filled into ten capsules, and it was determined that it was possible to fill the capsules to contain 590 mg. of ingredients (665 mg. of total weight of the encapsulated products). This experiment therefore confirmed that capsule grade APAP was usable and that acceptable solid encapsulated products could be prepared therefrom.

EXAMPLE 7

In this experiment, the ability of a composition in accordance with the present invention to form tablets was further tested. Accordingly, 5 kg. of capsule grade APAP was blended with 250 grams of Carbowax 8000 on a production Triumph blender. The resulting mixture was placed in three containers and held for 3 hours to melt the Carbowax 8000. Thereafter, each of the quantities of mixture were re-blended, heated and placed in trays to solidify.

After solidification was complete, the material was pressed through a 30 mesh screen to form a granulation. The granulation was then placed in a hopper, and its weight was adjusted to 580 mg. Tablets were thereafter formed and were found to be acceptable in hardness and disintegration.

EXAMPLE 8

Further blends of direct compression formulations were prepared as follows:

TABLE 2

| INGREDIENTS | FORMULATION (in grams) | |
|---|---|---|
| | A | B |
| Dense - APAP | 500 | 500 |
| Carbowax 8000 | 52.6 | 55.6 |

Formulation A reflected a 5% matrix content, while formulation B represented a 10% matrix content.

The materials as above formulated were each blended in a laboratory scale Hobart mixer, after which they were subjected to melting temperatures of 60° C. and spread on an aluminum tray, cooled to harden, and then pressed through a 30 mesh screen. The resulting granular material was then tableted on a rotopress. The material formed tablets easily, then yielded acceptable hardness of 6+ kg. (in elongated tablet) and disintegrated within 8 minutes 15 seconds for the 5% blend and 5 minutes 10 seconds for the 10% blend.

The same formulations indicated above were prepared with 2% Ac-Di-Sol and were then tableted on a layer press. The resulting tablets were excellent in hardness and other properties, and disintegrated in less than one minute.

Further formulations for tableting containing 5%, 10%, 15% and 20% matrix material were prepared as above, including 20% by weight of caffeine, each of the granulations, blending the same and the test tableting. The 5% blend did not produce good tablets, while the 10% blend produced acceptable tablets and the 15% and 20% blend produced good tablets with the 20% blend being the best. Disintegration of these products was slow but was under 30 minutes. It was theorized that a granulation containing 30% Carbowax and APAP would accommodate a higher level of a contaminant such as caffeine in a bulk granulation of this kind.

Moreover, the experiments regarding tableting illustrated that a broad range of matrix concentrations for direct tableting was possible, depending upon the remainder of the material in the composition.

EXAMPLE 9

A further tableting blend containing a material known as CONPAP, Ac-Di-Sol, sodium lauryl sulfate and lactose was prepared for direct tableting at a level of 600 mg. per unit using a capsule shaped punch and die. The tablets thus formed were excellent, disintegrated in less than 2 minutes. Thereafter, the same composition was prepared as a core for a size No. 1 capsule. The cylindrical tablets after formation were then forced into capsules, capped and sealed in a microwave oven at full power for 45 seconds, using methanol as a sealing or dielectric fluid. The resulting product was superior to commercially available products formed by similar procedures but had superior outer appearance.

EXAMPLE 10

Further compositions were prepared in accordance with the present invention to evaluate alternative matrix materials. Accordingly, sorbitol and mannitol were prepared in separate mixtures in the following fashion.

TABLE 3

| INGREDIENTS | FORMULATION (in grams) | |
|---|---|---|
| | C | D |
| APAP - Dense | 100 | 100 |
| Sorbitol | 17.6 | |
| Mannitol | | 17.6 |

The above compositions were then blended and heated until the respective matrix materials melted. The materials were then blended again, and each was pressed into size No. 1 capsules and weighed. The respective capsules when filled weighed 650 mg. in each instance, indicating that 575 mg. of weight were attributable to the ingredients. The products were then cooled and were found to be hard, with sorbitol, however, offering greater resistance to pulverization under pressure. It was therefore determined that higher quantities of both sorbitol and mannitol in the mixture would improve hardness of these capsule cores.

The materials prepared above were prepared as granulations which were then spread on trays, cooled, passed through a 30 mesh screen and then tableted on a layer press. The resulting tablets were desirably hard and possessed the remainder of the favorable properties hereof.

EXAMPLE 11

In this example, a composition was prepared which included the medicament acetaminophen together with 90% APAP and 10% Carbowax 8000. This preparation was physically mixed to form a flowable powdered mixture, and the powdered mixture was then introduced into several Size 1 capsules with intermittent tamping, as would be conducted with a conventional tamp-filling machine, and when the capsules were filled, they were closed. In the present instance, locking capsule halves were utilized and the larger cap was placed over the smaller diameter cap until they locked into position with each other. The capsules were weighed, and it was determined that a maximum of 490 mg. of fill weight was achieved.

Two such capsules were then placed in a microwave oven which was set on an intermittent cycle, and they were heated until the contents of the capsule melted. The heating cycle was approximately 2.3 minutes in duration. Under these conditions, the capsule bodies did not melt or deform, and upon cooling, the resulting capsules contained a hard core as desired. Upon opening and inspecting the capsules, the core was noted to be somewhat honeycombed, and it was thereby determined that a denser filling was desirable.

EXAMPLE 12

Two further capsules prepared in accordance with the procedure set forth in Example 11 were heated in an alternative fashion by placing in a convection oven and exposed to a temperature of about 65° C. for a period of time until melting was observed. The capsules were inspected, and it was found that they did not deform at this temperature. Thereafter, the capsules were cooled to room temperature. After cooling was complete, the capsules were opened and inspected, and it was noted that the cores were solid but were honeycombed as indicated above.

EXAMPLE 13

Two additional capsules were placed into an encapsulating ring and were then heated to 70° C., to melt the matrix and permit solidification of the core to commence. The encapsulating ring was permitted to stand until it cooled, at which time the capsules were removed and were opened for inspection. In similar fashion to the previous examples, the cores were noted to be solid but somewhat honeycombed.

EXAMPLE 14

In this example, a modification to the method of Example 11 was implemented to achieve a denser core. Accordingly, a hollow capsule half was placed in a capsule ring which had been heated to 60° C. The flowable mixture was itself heated to 58° C. and was then incrementally introduced into the hollow capsule with intermittent tamping by a heated metal rod corresponding to the tamping rod in the conventional tamp-filling capsule machine. The rod had been heated to 90° C. and was brought into contact with the powdered core material at each instance after a quantity of such material was introduced into the capsule. This procedure was conducted within an oven and was performed repeatedly until the capsule body was full. A small portion of the same blend was placed into the capsule cap, and it was likewise tamped down with application of heat.

The cap and the remainder of the capsule body were then closed, and the capsule bodies were removed and allowed to cool. The final weight of the capsules was 570 mg., and the core was completely solid. Upon visual inspection of the contents of the capsule, it was found that a desirably dense and solid core had been prepared.

While the present disclosure has proceeded with reference to particular matrix materials such as those listed earlier, it is to be understood that other matrix materials are likewise usable. For example, suitable matrix materials also contemplated in accordance with the present invention comprise polymerizable materials that thermoset for time release and thereafter dissolve in body fluid or enzymes. These materials may be used in conjunction with the matrix materials listed above to achieve variations in the time of release of the active ingredient.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for preparing a solid, tamper evident encapsulated product capable of peroral delivery without delay of a medicament or other edible active ingredient, comprising:
   a. preparing a flowable mixture comprising at least one orally administrable medicament in an ingestible matrix material having a melting point ranging up to about 100° C.;
   b. introducing the mixture of Step a. into an ingestible hollow capsule in an amount sufficient to substantially completely fill the interior thereof;
   c. heating the capsule containing the mixture of Step b. to a temperature sufficient to liquify said matrix material;
   d. solidifying the mixture in the sealed capsule of Step c. to form said solid encapsulated product; and
   e. sealing the capsule of Step d.;
   wherein said mixture and said capsule in said solid encapsulated product are integral with each other, and together cause said solid encapsulated product to be tamper-evident.

2. The method of claim 1 wherein said matrix material is selected from the group consisting of carbohydrates, polyalkylene glycols, polyoxyalkylene glycols, and mixtures thereof.

3. The method of claim 2 wherein said matrix material is selected from the group consisting of polyethylene glycol, polyethylene glycol ether, sugars, sugar alcohols, gelatin and mixtures thereof.

4. The method of claim 3 wherein said matrix material is selected from the group consisting of sorbitol, mannitol, mannose, gelatin, and polyethylene glycols having a molecular weight in the range of from about 6,000 to about 20,000, polyoxyethylene glycols, and mixtures thereof.

5. The method of claim 1 wherein said matrix material is present in an amount of up to about 35% by weight.

6. The method of claim 5 wherein said matrix material is present in an amount of from about 5% to about 35% by weight.

7. The method of claim 6 wherein said matrix material is present in an amount of from about 10% to about 20% by weight.

8. The method of claim 4 wherein said matrix material comprises a polyethylene glycol having a molecular weight of from about 6000 to about 20,000 in an amount of from about 5% to about 20% by weight.

9. The method of claim 8 wherein said matrix material comprises a mixture of a polyethylene glycol having a molecular weight of from about 6,000 to about 20,000, and gelatin.

10. The method of claim 4 wherein said matrix comprises a mixture of said polyethylene glycol and said gelatin and is present in a total amount of from about 5% to about 20% by weight.

11. The method of claim 4 wherein said matrix comprises sorbitol.

12. The method of claim 4 wherein said matrix comprises mannitol.

13. The method of claim 1 wherein said matrix includes an edible, water soluble melting point modulator.

14. The method of claim 1 wherein the mixture of Step a. is preheated to a temperature below the melting point of said matrix prior to Step b.

15. The method of claim 1 wherein Step b. is performed by alternately introducing an increment of said mixture into said capsule and thereafter tamping said increment to compact the same.

16. The method of claim 15 wherein said mixture is compacted with a tamping rod heated to a temperature sufficient to melt said matrix.

17. The method of claim 15 wherein said mixture is introduced into both halves of said hollow capsule.

18. The method of claim 1 wherein the capsule is pretreated before Step b. by wetting the interior surface thereof followed by dusting the wetted interior surface with a quantity of granular gelatin in an amount sufficient to roughen said interior surface.

19. The method of claim 1 further including the step of treating the encapsulated product at Step e. by application of thermal energy to seal the said capsule halves to each other and to said solid composition.

* * * * *